United States Patent [19]

Berstermann

[11] 4,102,573
[45] Jul. 25, 1978

[54] ELECTRODE FOR A SPECTRO-ANALYTICAL ARRANGEMENT

[75] Inventor: Wilhelm Berstermann, Georgsmarienhutte, Fed. Rep. of Germany

[73] Assignee: Klockner-Werke AG, Duisburg, Fed. Rep. of Germany

[21] Appl. No.: 771,796

[22] Filed: Feb. 24, 1977

[30] Foreign Application Priority Data

Feb. 25, 1976 [DE] Fed. Rep. of Germany ....... 2607596

[51] Int. Cl.² .................................................. G01J 3/30
[52] U.S. Cl. ..................................................... 356/86
[58] Field of Search ........................................... 356/86

[56] References Cited

U.S. PATENT DOCUMENTS

| 3,711,201 | 1/1973 | Sturlese et al. | 356/86 |
| 3,942,892 | 3/1976 | Ambrose et al. | 356/86 |

Primary Examiner—Vincent P. McGraw
Attorney, Agent, or Firm—Michael J. Striker

[57] ABSTRACT

An electrode for a spectro-analytical arrangement is of a substance consisting of carbonaceous and metallic components so that an envelope of reducing atmosphere surrounds an electric spark discharge generated between an electrode and a metallic body the composition of the material of which is to be spectro-analytically determined. The substance may be a homogeneous mixture of the carbonaceous and metallic components, such as a sintered mixture of pulverulant metallic and carbonaceous metals. The particles of the metallic component have sizes of at most 0.1 millimeter, while the particles of the carbonaceous component have sizes at most 0.01 millimeter. The carbonaceous component may be graphite, while the metallic component may be silver. The amount of graphite in the substance may be between 5 and 20% by weight and the amount of silver may be between 95 and 80% by weight. The preferred use of the electrode of the invention is in a spectral quantometer.

10 Claims, 4 Drawing Figures

ELECTRODE FOR A SPECTRO-ANALYTICAL ARRANGEMENT

CROSS-REFERENCE TO RELATED APPLICATIONS:

The present invention is related to copending, commonly owned U.S. patent applications Ser. Nos. 655,770; 665,771, now U.S. Pat. No. 4,037,962; 665,772, now U.S. Pat. No. 4,037,963; 665,773 and 665,774, all filed on Mar. 10, 1976.

BACKGROUND OF THE INVENTION:

The present invention relates to an electrode for use in an arrangement for spectro-analytically determining the composition of materials, particularly metallic alloyed materials.

The principles of spectro-analysis are so well known that they need no detailed discussion here. The field which is of primary concern for the present invention is that where an electric spark discharge is passed between a conductive workpiece to be tested and an electrode.

It is known to examine workpieces or similar bodies for their compositions by generating a unipolar or single-polarity pulse or spark discharge between a sample of such workpiece which is in contact with an electrode, and a counterelectrode spaced from the sample. The spark is luminous and emits light in both the visible and ultraviolet spectrum, which light can be then divided into spectral lines each of which is indicative of the presence of an alloying element present in the workpiece, while the intensity of each line represents the quantity or percentage of that component in the material of the workpiece. Thus, a spectrometer working with such a spark-discharge arrangement can perform an exact quantitative and qualitative analysis of the composition of the material of the alloyed workpiece.

Such a spectro-analytical examination finds its most prominent use in the steel-manufacturing and related industries wherein it is very often desired to determine whether or not the alloyed materials being produced or stored conform in their composition to predetermined percentages of various alloying elements. As already mentioned previously, this is accomplished, more often than not, by taking samples from the workpieces the composition of which is to be determined, and by testing such samples in laboratories both qualitatively and quantitatively by means of spectrometers. The sample and the counterelectrode are brought to a high potential differential so that a spark discharge occurs between the sample and the counterelectrode. Then, the luminous emission of the spark discharge is transformed into a spectrum by means of a diffractive grating, which spectrum is then evaluated. The chemical elements which are present in the material of the sample are indicated by the presence of emission or absorption lines at corresponding zones of the spectrum. The intensity of each of the spectral lines is a measure for the percentage of the particular element in the alloyed material, and such percentages can be established in an optical and electronic manner such as by resorting to the use of integrating capacitors.

Inasmuch as a device for producing high potentials is necessary for generating the spark discharge and thus the luminous emission which is then deflected to form the spectrum, it is necessary generally speaking, to attend to complex protective measures so as to protect the operating personnel from the existing high voltages. Inasmuch as a part of the spectral lines to be detected is located in the short-wave ultraviolet region of the spectrum, it is necessary to so construct the arrangement as to be not only secure in terms of the high voltage, but also at least a part of the arrangement which embraces the path of the luminous rays from the spark discharge location to at least the deflective grating must be capable of being evacuated. These requirements have resulted in a situation in which these arrangements, which are designated as quantometers, necessarily have large dimensions and a corresponding weight and, for these reasons, they must be constructed for stationary mounting, that is, they can only be used when immovably mounted in a laboratory.

In addition thereto, there have also been already proposed, for the production of the reflective spectrum, Rowland spectrometers which are possessed of the advantage that the images of the spectrum lines are located in a so-called Rowland circle. In the currently available quantometers, the Rowland circle has a substantial diameter, inasmuch as the so-called primary slit which acts as an ingress pupil and serves to create an image of the spark discharge on the Rowland grating, must be adjustable in its position. One of the primary reasons for selecting the large diameter of the Rowland circle is that the short circular arc in which the primary slit is to be adjusted can be regarded, in the first approximation, as being a straight line, so that the primary slit can be provided in an element mounted on a carrier arm for pivoting eccentrically to the center of the Rowland circle, and the position thereby can be adjusted by pivoting such carrier arm. For this reason, analyzers must have considerable dimensions and used in a stationary manner, even in the event that they are operated exclusively in the visible range of the spectrum and, therefore, the above-mentioned evacuation is dispensed with.

In many instances, however, one is interested in a constant supervision of the composition of the material, wherein only the maintaining of the proper percentage of, for instance, silicone, chromium, molybdenum, and so on is to be examined, that is, the material is to be examined for elements the spectral lines of which to be monitored lie in the visible and long-wave ultraviolet part of the spectrum, so that evacuated arrangements need not be employed. This is, for instance, the case when batches of tied rod material with predetermined proportions of chromium, molybdenum and so on in their material are to be examined for the presence of eroneously sorted rods having materials of different composition, and such improper rods are to be sorted out of the respective batch.

Especially under these circumstances, the testing of each rod by severing a disc-shaped end portion therefrom and testing such severed end portion in a quantometer, is too laborious and expensive a procedure and, from a certain number of the rods upward, it is not economically feasible and thus cannot be resorted to, so that it was heretofore customary under such circumstances to utilize random sampling techniques which, of course, are highly unreliable in most circumstances.

There have also already been proposed hand-held spectroscopic devices to be used for random-sample monitoring without taking samples, which render it possible to approximately examine the composition of the material being examined by visual observation of the spectrum which is deflected by prisms. In this arrangement, however, a very high degree of skill and experience is required for properly associating the respective spectral lines with various elements. Even then, however, the visual perception is inadequate to perceive the variations in the intensities of the various spectral lines, which result from different proportions of the respective element in the material being tested.

The generation of the electric spark discharge may be accomplished by means of bipolar excitement, but under these circumstances, material evaporates both from the sample of the material being tested and from the electrode. Such material then deposits on the sample being tested, on the one hand, but also on the counterelectrode, on the other hand, so that when the next-following sample is being tested, to determine the spectral analysis of such sample, the material previously deposited on the counterelectrode will also produce a spectrum and thus partially influence the spectrum of the material of the sample being tested, so that misleading results, in terms of spectral lines, may be obtained.

In order to avoid evaporation of the material of the counterelectrode, it is further known to trigger a unipolar electric spark discharge, in which a deposition of vaporized material on the electrode can be avoided.

An apparatus of conventional nature which employs this concept is possessed of the above-discussed disadvantages, particularly in view of the fact that a material sample must be taken from the material to be examined, and such sample must be examined in a laboratory by means of the analyzer present therein.

In order to be able to achieve a constant super-vision without sample taking of, for instance, tight bundles of rod material, these has already been proposed an analyzer of the portable type. The details of such a portable analyzer can be found in the above-mentioned commonly owned patent applications. Such a portable analyzer is transported to a storage area where the rods to be tested are stored and then an electric spark discharge is generated between a respective end face of one of the rods and the electrode which is held at a predetermined distance from the end face by means of a sleeve, with resulting formation of a spectrum. Such spectrum is then evaluated and thus all of the above-mentioned rods can be tested in a relatively short period of time.

In the conventional arrangement a hardened area is produced at that region of the rod or other workpiece being examined where the spark discharge jumps over. However, such hardening is most undesirable, especially because, generally speaking, the affected end portions, however short, are unusable during the further machining or other treating of the rods. In principle, these hardened areas could be grinded, milled or otherwise machined away, or the affected end portions could be cut away and discarded. However, under these circumstances, the constant supervision or testing would be rendered prohibitively cumbersome and expensive.

When the electric spark discharge occurs in the ambient atmosphere, the above-mentioned hardening is rendered even more pronounced by the formations of a flowable slag ball at the point of impingement of the spark discharge, which is additionally a preferred and prominant point for the spark discharge to travel to. A result of this is that, in addition to the more pronounced hardening, there obtains as a further undesired effect a reduction in the accuracy of the analysis.

Such hardening also occurred in the prior art where samples are being tested, but did not have any detrimental consequences inasmuch as each of the samples was discarded after the performance of the analysis.

SUMMARY OF THE INVENTION

Accordingly, it is a general object of the present invention to avoid the disadvantages of the prior art.

More particularly, it is an object of the present invention to provide an electrode for use in a spectro-analytic apparatus which is not possessed of the above-discussed disadvantages.

A further object of the present invention is to so construct the spectro-analytic apparatus as to avoid the formation of the hardened areas during the testing operation performed thereby.

A concomitant object of the present invention is to provide a spectro-analytic apparatus which is capable of working with only minimum dispersion of the sensed values.

Yet another object of the present invention is to provide an electrode for use in such an apparatus which is more durable than known before.

In pursuance of these objects and others which will become apparent hereafter, one feature of the present invention resides, in an arrangement for spectro-analytically determining the compositions of the material of metallic bodies using an electric spark discharge between an electrode and a respective metallic body, briefly stated, in the improvement wherein the electrode is of a substance consisting of carbonaceous and metallic components. Preferably, such substance is a homogeneous mixture of such components and, advantageously, the electrode is an elongated sintered rod of pulverulent particles of such component. More particularly, the invention resides in an arrangement for spectro-analytically determining the composition of the material of a metallic body comprising, in combination, a sintered electrode of a mixture of pulverulent carbonaceous and metallic particles; means for generating an electric spark discharge between the electrode and a metallic body the composition of the material of which is to be determined, and means for analyzing the spectrum of light emitted during the spark discharge.

As a result of the composition of the substance of the electrode, it is achieved that the electric spark discharge is performed in a reducing atmosphere. In a current preferred advantageous embodiment of the present invention, excellent results are obtained when the spark discharge is strongly damped by accordingly designing the circuit which generates the electric spark discharge.

As a result of these measures, the formation of slag which is customary when the electric spark discharge is conducted in an oxidizing atmosphere is avoided, as a result of which, on the one hand, the danger of hardening the respective zones of the workpiece or body is substantially reduced, and, on the other hand, the accuracy of the measurement is improved.

Several-hundred spark discharges can be performed with the electrode according to the present invention, without mutual influencing of the individual measurements.

Optimum results are obtained, according to the present invention, when graphite is used as the carbonaceous component. The amount of graphite in the above-mentioned substance may be between 5 and 20% by weight and the amount of the metallic component may be between 95 and 80% by weight. Preferably, the range of the amount of graphite in the substance is between 6 and 12% by weight.

The particles of the metallic component preferably have sizes at most equal to 0.1 millimeter, while the particles of the carbonaceous component have sizes at most equal to 0.01 millimeter. Advantageously, the metallic component is silver.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
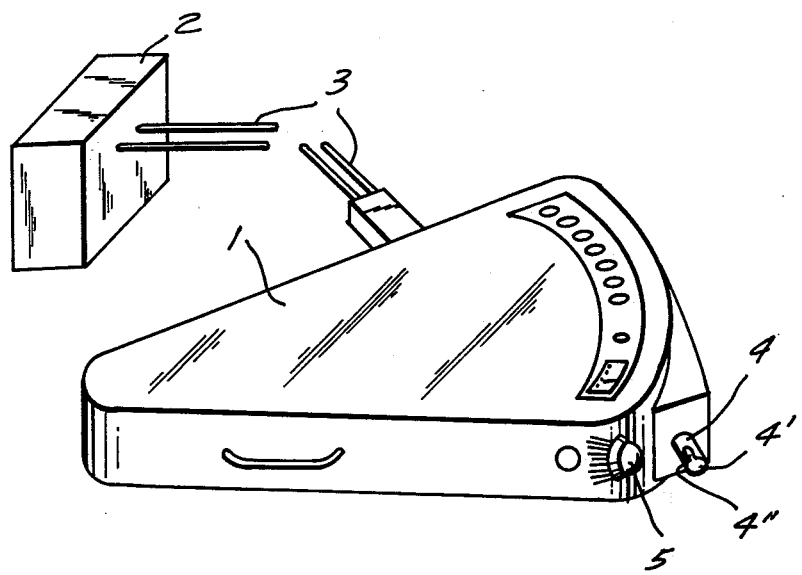
FIG. 1 is a perspective view of a spectro-analytic apparatus in which the present invention is used.

Referring now to the drawings in detail, and first to FIG. 1 thereof, it may be seen that it illustrates a portable spectro-analytical apparatus 1 to which high-energy direct current is supplied from a source of such current through wires 3. Details of the source 2 and of the analyzer 1 have already been disclosed in the commonly owned copending patent application Ser. Nos. 665,770; 665,771, now U.S. Pat. No. 4,037,962; 665,772, now U.S. Pat. No. 4,037,963; 665,773 and 665,774, so that they will be discussed here only to the extent necessary for understanding the present invention. The analyzer 1 has a contact sleeve 4 having an open end 4' and a lateral opening 4' which opens toward an entrance window 5 into the interior of the analyzer 1.

Figure 2:
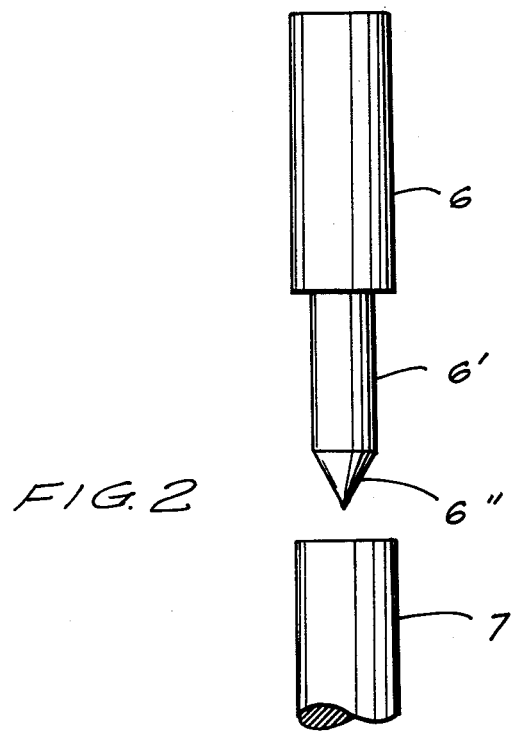
FIG. 2 is a side elevational view of an electrode of the present invention as juxtaposed with a body to be tested.

Referring now to FIG. 2, it may be seen that an electrode 6 according to the present invention has a portion 6' of reduced diameter which merges into a converging tip portion 6'' which is to be juxtaposed with a workpiece 7 to be tested. The electrode 6 is mounted in the sleeve 4 in a manner illustrated in FIG. 3, which is also discussed in detail in one of the above-mentioned patent applications. For purposes of understanding the present invention, it is sufficient to say that the wire 3 supplies the spark-over voltage to the electrode 6 so that a spark discharge is generated between the tip portion 6'' and the workpiece 7 to be tested through the open 4' of the sleeve 4. The luminous waves emitted by the spark discharge leave the interior of the sleeve 4 through the open side 4'' thereof and reach the interior of the analyzer 1 through the inlet window 5 which is in registry with the open side 4'' as illustrated in FIG. 1. The luminous waves are then defracted in the interior of the analyzer 1 into a spectrum which is then evaluated in a manner fully disclosed in the above-mentioned patent applications.

The electrode of FIG. 2 consists of a sintered mixture of, for instance, 10% by weight of graphite and 90% by weight of silver. The proportion of the carbonaceous component of the mixture, such as graphite, may be between 5 and 20% by weight, but preferably is in the range between 6 and 12% by weight. While silver is a preferred metallic component of the mixture, other metals of properties similar to those of silver may also be used, provided however that these metals are not such the presence of which in the material of the workpiece 7 to be tested is to be detected.

To obtain the electrode 7, graphite available in pulverulent form, having particles sizes of less than 0.1 millimeter is mixed with silver particles having particle sizes of less than 0.01 millimeter to obtain an intimate mixture of such particles. Such mixture is then shaped into the configuration of the electrode 6 and compressed with a pressure of approximately 20 kilograms per square centimeter. Following such compression, the thus-obtained body is sintered in a heating oven at a temperature of 750° C for approximately 2 hours and in a reducing atmosphere.

Figure 4:
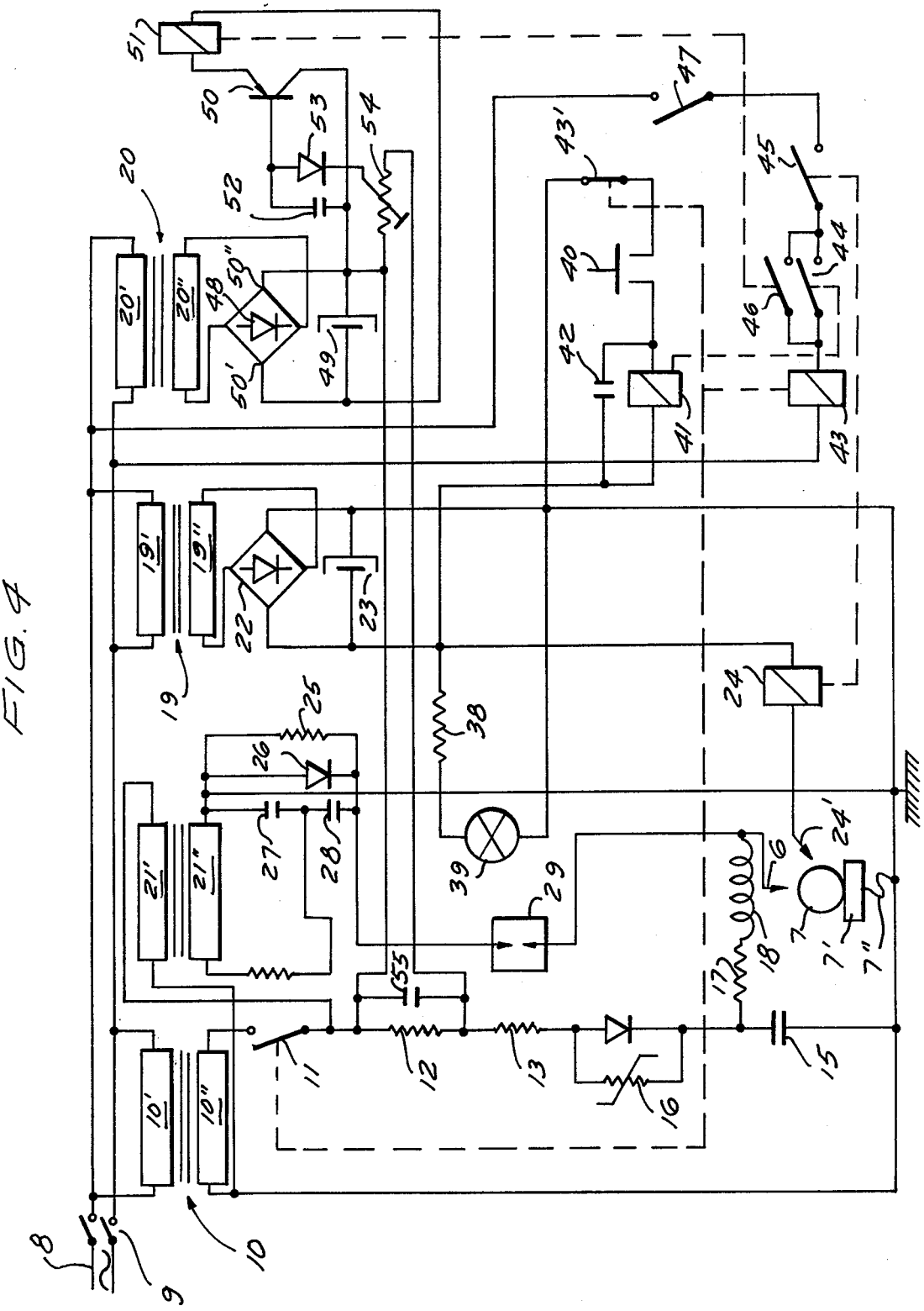
FIG. 4 is an example of a circuit diagram which can be used in an apparatus of FIG. 1 for generating an electric spark discharge between the electrode of FIG. 2 and the workpiece.

FIG. 4 illustrates an example of a circuit diagram of a power-supply arrangement which may be used for generating a spark discharge across the gap between the electrode 6 and the workpiece 7. It includes three transformers 10, 19 and 20 which have their primary windings 10', 19' and 20' connected in parallel to an alternating current line 8 via a double-pole single-throw on-off switch 9. The high-voltage secondary winding 10'' of the transformer 10 is connected to a first loop in which there is provided a normally-open switch 11, a pair of series-connected resistors 12 and 13, a diode 14 and a condenser 15. A varistor 16 is connected in parallel across the diode 14.

Connected in parallel across the condenser 15 are, in series, a resistor 17, an induction coil 18, the electrode 6, a workpiece 7, another electrode 7' and a grounding cable 7''. The electrode 6 is spaced by a gap from the workpiece 7 which lies in good electrical contact with the base or contact electrode 7'. The coil 18 may be wound using resistance wire in order to eliminate the resistor 17. It should be clear that, when switch 11 is closed, a unipolar pulse will be fired across the gap between the electrode 6 and the workpiece 7.

Another transformer 21 is connected across the secondary winding 10'' of the transformer 10 so that its primary winding 21' is only energized when the switch 11 is closed. The secondary winding 21'' of this transformer 21 is connected to a voltage-doubling circuit comprising, in parallel, a resistor 25, a diode 26, and a pair of series connected capacitors 27 and 28 between which there is connected a resistor 25' connected to one side of the secondary winding 21'. The other side of the secondary winding 21'' is grounded. The high-voltage output from this circuit 25–28 is fed to an auxiliary spark gap 29 connected to the electrode 6. Thus, the closing of the switch 11 will cause a high-voltage unipolar pulse to pass between the electrode 6 and the workpiece 7, provided that the workpiece 7 is in good electrical contact with the base electrode 7'.

The secondary winding 19' of the transformer 19 is connected to a full-wave rectifier bridge 22 across which there is connected a smoothing capacitor 23. One side of this full-wave rectifier 22 is connected to one side of a relay coil 24 the other side of which is connected to a test terminal 24' engageable with the workpiece 7. The other side of the full-wave rectifier 22 is grounded. In addition thereto, there is connected across this low-voltage power supply a mercury-vapor lamp 39 in series with a resistor 38 for pre-ionizing the auxiliary gap 29. The terminal 24' must be in good electrical contact with the workpiece 7 which, in turn, must be in good electrical contact with the electrode 7', in order for the low-voltage loop to be closed and for current to pass through the coil 24.

Also connected across the full-wave rectifier 22 of the low-voltage power source is a third loop constituting a momentary-contact push-button switch 40 connected in series between a normally-closed switch 43' and a relay coil 41. A condenser 42 is connected across this coil 41 which serves to maintain electrical energizaion of this coil 41 for a limited period of time after either of the switches 40 or 43' is opened.

A relay coil 43 is also connected across the line in series with two normally open switches 44 and 45. The switch 44 is operated by the relay coil 41 and the switch 45 by the relay coil 24. At the same time, the coil 43 operates the normally-closed switch 43' and the normally-open switch 11. Another normally-open switch 46 is also connected across the switch 44. A time-control switch 47 which is connected to a control circuit is also connected in series with the coil 43 so that this coil 43 can only be electrically energized when the switches 47 and 45 are closed as well as one of the switches 44 and 46.

The transformer 20 has a secondary winding 20" connected to a bridge circuit 48 having a pair of outputs 50' and 50" across which there is connected a smoothing arrangement 49. A transistor 50 has its collector connected to the terminal 50" and its emitter connected through a load constituted by a relay coil 51 to the terminal 50'. The base of this transistor 50 is connected via a capacitor 52 to terminal 50" and through a diode 53 to the tap of the potentiometer 54 connected across the resistor 12 of the third loop. A capacitor 55 is also connected across the resistor 12 to smooth out the voltage changes thereacross. When current flows through the resistor 12, it is detected by the transistor 50 which actuates the coil 51 which, in turn, operates and closes the switch 46.

Figure 3:
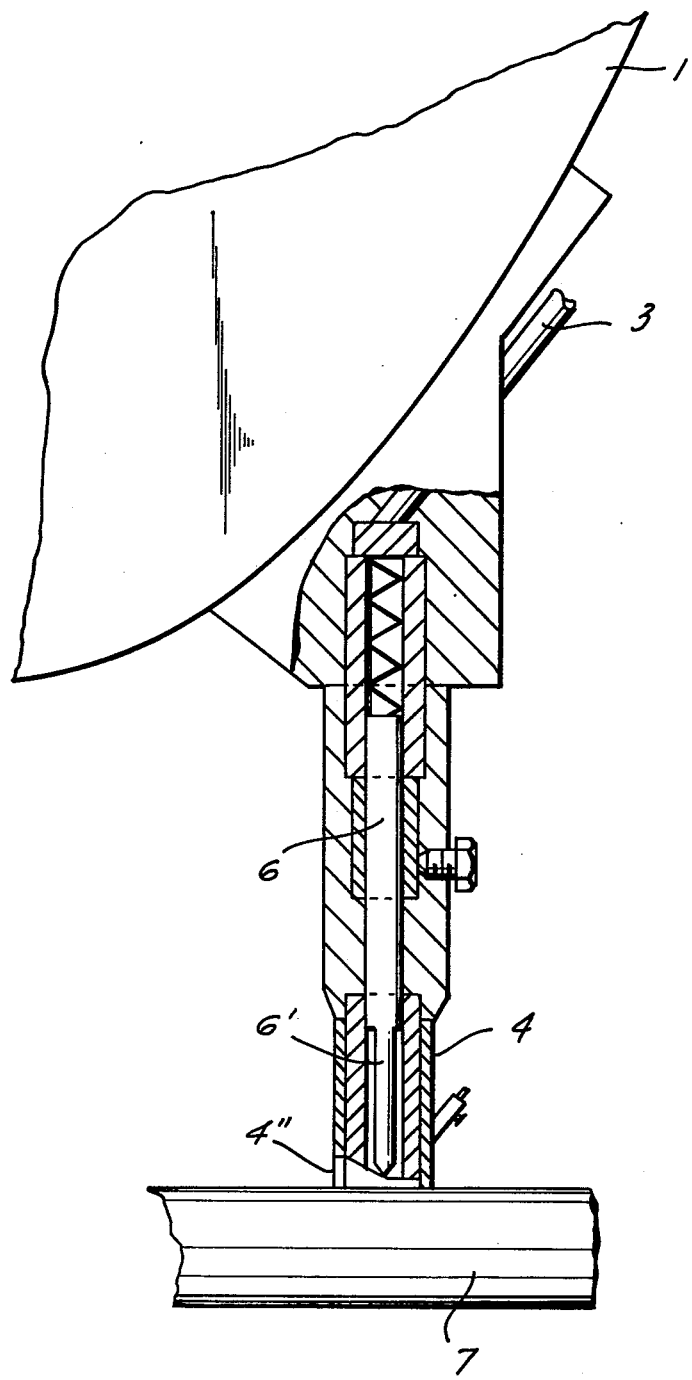
FIG. 3 is a partially section view illustrating how the electrode of FIG. 2 is mounted on the apparatus of FIG. 1.

While the contacts 7' and 24' have been illustrated as separate elements, it is to be understood that the function thereof may be performed by parts of the sleeve 4 illustrated in FIG. 3.

The function of the above-described circuit is fully discussed in the above-mentioned copending, commonly owned patent application Ser. No. 665,772, now U.S. Pat. No. 4,037,693, to which reference is being had for detail. For the purposes of understanding the present invention, it is sufficient to know that the loops energized by the transformers 10 and 21 will generate the spark-over voltage, and that the remainder of the circuitry will assure that no spark will jump across the gap between the electrode 6 and the workpiece 7 unless there is good electric contact between the electrode 24' and the workpiece 7, on the one hand, and between the workpiece 7 and the electrode 7', on the other hand, which, in its practical application, means that the sleeve 4 is in good electrical contact with the workpiece 7.

It is to be understood that the above-discussed circuit is an example only of a source of high-voltage which can be used for generating the potential differential between the electrode 6 of the present invention and the workpiece 7, and that the electrode 6 can be used in connection with other sources of high volage, whether working on a unipolar or bipolar basis. Also, the electrode of the present invention can be used in connection with spectrum-analyzing devices of a different type from that illustrated in FIG. 1.

However, the electrode 6 of the present invention finds its most advantageous use in the environment described above, particularly where the high-voltage source supplies only unipolar pulses. Under these circumstances, the electric spark discharge will be performed in a reducing atmosphere, and the evaporated material of the workpiece 7 will not deposit on the electrode 6 where it would otherwise influence the test results in subsequent testing or analyzing operations.

It will be understood that each of the elements described above, or two or more together, may also find a useful application in other types of constructions differing from the types described above.

While the invention has been illustrated and described as embodied in an electrode for use in spectro-analysis apparatus, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an arrangement for spectro-analytically determining the compositions of the materials of metallic bodies using an electric spark discharge between an electrode and a respective metallic body, the improvement wherein the electrode is of a substance consisting of carbonaceous and metallic components.

2. The improvement as defined in claim 1, wherein said substance is a homogeneous mixture of said components.

3. The improvement as defined in claim 2, wherein said electrode is an elongated sintered rod of pulverulent particles of said components.

4. The improvement as defined in claim 3, wherein the particles of the metallic component have sizes at most equal to 0.1 millimeter.

5. The improvement as defined in claim 3, wherein the particles of the carbonaceous component have sizes at most equal to 0.01 millimeter.

6. The improvement as defined in claim 1, wherein the carbonaceous component is graphite.

7. The improvement as defined in claim 4, wherein the amount of graphite in said substance is between 5 and 20 percent by weight and the amount of the metallic component is between 95 and 80 percent by weight.

8. The improvement as defined in claim 7, wherein the amount of graphite is between 6 and 12 percent by weight.

9. The improvement as defined in claim 1, wherein the metallic component is silver.

10. An arrangement for spectro-analytically determining the composition of the material of a metallic body comprising, in combination, a sintered electrode of a mixture of pulverulent carbonaceous and metallic particles; means for generating an electric spark discharge between said electrode and a metallic body the composition of the material of which is to be determined; and means for analyzing the spectrum of light emitted during the spark discharge.

* * * * *